US010772644B2

(12) United States Patent
Feltyberger et al.

(10) Patent No.: US 10,772,644 B2
(45) Date of Patent: Sep. 15, 2020

(54) ASPIRATION SYSTEM FOR THROMBECTOMY PROCEDURES

(71) Applicant: Rex Medical, L.P., Conshohocken, PA (US)

(72) Inventors: Daniel Stephen Feltyberger, Blairstown, NJ (US); Marc-Alan Levine, Pottstown, PA (US)

(73) Assignee: Rex Medical L.P., Conshohocken, PA (US)

( * ) Notice: Subject to any disclaimer, the term of this patent is extended or adjusted under 35 U.S.C. 154(b) by 538 days.

(21) Appl. No.: 15/482,662

(22) Filed: Apr. 7, 2017

(65) Prior Publication Data

US 2017/0209161 A1  Jul. 27, 2017

Related U.S. Application Data

(63) Continuation of application No. 14/550,941, filed on Nov. 22, 2014, now Pat. No. 10,219,814.
(Continued)

(51) Int. Cl.
*A61B 17/22* (2006.01)
*A61M 1/00* (2006.01)
(Continued)

(52) U.S. Cl.
CPC ...... *A61B 17/22* (2013.01); *A61B 17/320758* (2013.01); *A61M 1/008* (2013.01); *A61M 1/0019* (2013.01); *A61M 1/0023* (2013.01); *A61M 25/0662* (2013.01); *A61M 39/06* (2013.01); *A61M 39/22* (2013.01); *A61B 2017/00115* (2013.01); *A61B 2017/00734* (2013.01); *A61B 2017/22079* (2013.01);
(Continued)

(58) Field of Classification Search
CPC .. A61M 1/0019; A61M 1/008; A61M 1/0023; A61M 25/0662; A61M 39/06; A61M 39/22; A61B 17/22; A61B 17/320758
See application file for complete search history.

(56) References Cited

U.S. PATENT DOCUMENTS

| | | | |
|---|---|---|---|
| 4,029,097 A | 6/1977 | Leroy | |
| 4,324,243 A | 4/1982 | Helfgott et al. | |

(Continued)

FOREIGN PATENT DOCUMENTS

| | | |
|---|---|---|
| WO | WO 87/01276 | 3/1987 |
| WO | WO 98/34673 | 8/1998 |
| WO | WO 2013/022796 | 2/2013 |

OTHER PUBLICATIONS

The European Search Report dated Feb. 3, 2015 for International Application 14196918.8.

*Primary Examiner* — Ariana Zimbouski
(74) *Attorney, Agent, or Firm* — Neil D. Gershon (57) ABSTRACT

An aspiration system including a housing containing an aspiration pump, a chamber, a collection bag in fluid communication with the chamber, and a tubing assembly including a first tube portion connected to the chamber. The tubing assembly has a connector to split the first tube portion into a second and third tube portion, the second tube portion in fluid communication with a first catheter to aspirate particles through the first catheter and the third tube portion in fluid communication with a second catheter to aspirate particles through the second catheter.

19 Claims, 11 Drawing Sheets

Related U.S. Application Data (60) Provisional application No. 61/916,034, filed on Dec. 13, 2013.

(51) Int. Cl.
*A61B 17/3207* (2006.01)
*A61M 25/06* (2006.01)
*A61M 39/06* (2006.01)
*A61M 39/22* (2006.01)
*A61B 17/00* (2006.01)

(52) U.S. Cl.
CPC .......... *A61B 2017/320733* (2013.01); *A61M 1/0068* (2014.02); *A61M 2039/229* (2013.01); *A61M 2205/3382* (2013.01); *A61M 2205/587* (2013.01); *A61M 2205/8206* (2013.01)

(56) References Cited

U.S. PATENT DOCUMENTS

| | | | |
|---|---|---|---|
| 4,504,263 A * | 3/1985 | Steuer | A61B 5/208 128/DIG. 13 |
| 4,883,476 A | 11/1989 | Kurtz et al. | |
| 5,078,683 A | 1/1992 | Sancoff et al. | |
| 5,176,502 A | 1/1993 | Sanderson et al. | |
| 5,273,526 A | 12/1993 | Dance et al. | |
| 5,446,229 A | 11/1995 | Elson et al. | |
| 5,662,627 A | 9/1997 | Say | |
| 5,766,191 A | 6/1998 | Trerotola | |
| 5,779,721 A | 7/1998 | Nash | |
| 5,843,103 A | 12/1998 | Wulfman | |
| 5,879,361 A | 3/1999 | Nash | |
| 5,938,672 A | 8/1999 | Nash | |
| 6,090,118 A | 7/2000 | McGuckin, Jr. | |
| 6,126,635 A | 10/2000 | Simpson et al. | |
| 6,319,242 B1 | 11/2001 | Patterson | |
| 6,652,495 B1 | 11/2003 | Walker | |
| 6,656,148 B2 | 12/2003 | Das et al. | |
| 6,843,797 B2 | 1/2005 | Nash et al. | |
| 6,905,505 B2 | 6/2005 | Nash et al. | |
| 7,037,316 B2 | 5/2006 | McGuckin et al. | |
| 7,063,688 B2 | 6/2006 | Say | |
| 7,160,273 B2 | 1/2007 | Greter et al. | |
| 7,276,052 B2 | 10/2007 | Kobayashi et al. | |
| 7,357,142 B2 | 4/2008 | Merkle | |
| 7,534,249 B2 | 5/2009 | Nash et al. | |
| D602,582 S | 10/2009 | Pidgeon et al. | |
| D602,584 S | 10/2009 | Pidgeon et al. | |
| 7,666,161 B2 | 2/2010 | Nash et al. | |
| 7,722,584 B2 | 5/2010 | Tanaka et al. | |
| 7,819,887 B2 | 10/2010 | McGuckin, Jr. et al. | |
| 7,833,239 B2 | 11/2010 | Nash | |
| 7,857,806 B2 | 12/2010 | Karpowicz et al. | |
| D630,313 S | 1/2011 | Pidgeon et al. | |
| D630,725 S | 1/2011 | Pidgeon et al. | |
| 7,867,191 B2 | 1/2011 | Suzuki | |
| 7,935,077 B2 | 5/2011 | Thor et al. | |
| 7,959,608 B2 | 6/2011 | Nash et al. | |
| 7,976,528 B2 | 7/2011 | Nash et al. | |
| 7,981,129 B2 | 7/2011 | Nash et al. | |
| 7,998,107 B2 | 8/2011 | Nash et al. | |
| D645,137 S | 9/2011 | Gonzalez | |
| D650,894 S | 12/2011 | Gonzalez | |
| 8,070,735 B2 | 12/2011 | Koch et al. | |
| 8,157,787 B2 | 4/2012 | Nash et al. | |
| 8,226,620 B2 | 7/2012 | Giezendanner et al. | |
| 8,240,470 B2 | 8/2012 | Pidgeon et al. | |
| 8,262,616 B2 | 9/2012 | Grant et al. | |
| 8,294,586 B2 | 10/2012 | Pidgeon et al. | |
| 8,409,160 B2 | 4/2013 | Locke et al. | |
| 8,430,837 B2 | 4/2013 | Jenson et al. | |
| 8,460,273 B2 | 6/2013 | Freedman et al. | |
| 8,491,523 B2 | 7/2013 | Thor et al. | |
| 8,500,706 B2 | 8/2013 | Michaels et al. | |
| 8,529,530 B2 | 9/2013 | Koch et al. | |
| 8,535,284 B2 | 9/2013 | Ramella et al. | |
| 8,579,851 B2 | 11/2013 | Cull | |
| 8,663,259 B2 | 3/2014 | Levine et al. | |
| 8,764,779 B2 | 7/2014 | Levine et al. | |
| 2002/0058915 A1 | 5/2002 | Wakabayashi | |
| 2002/0165567 A1 | 11/2002 | Shiber | |
| 2004/0230136 A1 | 11/2004 | Corrigan | |
| 2005/0065471 A1 * | 3/2005 | Kuntz | A61M 1/0023 604/133 |
| 2005/0087542 A1 * | 4/2005 | Bazbaz | A47F 9/042 221/33 |
| 2006/0253064 A1 * | 11/2006 | Gelfand | A61B 5/201 604/31 |
| 2008/0114301 A1 | 5/2008 | Bandhauer et al. | |
| 2009/0012485 A1 | 1/2009 | Michaels et al. | |
| 2010/0211030 A1 | 8/2010 | Turner et al. | |
| 2010/0286489 A1 | 11/2010 | Hartwell | |
| 2011/0028921 A1 | 2/2011 | Hartwell | |
| 2011/0071483 A1 | 3/2011 | Gordon et al. | |
| 2011/0112493 A1 | 5/2011 | Koch et al. | |
| 2011/0130730 A1 | 6/2011 | Hartwell et al. | |
| 2011/0190690 A1 | 8/2011 | Humayun et al. | |
| 2011/0300010 A1 | 12/2011 | Jarnagin et al. | |
| 2012/0157912 A1 * | 6/2012 | Sorensen | A61F 9/00745 604/28 |
| 2012/0289894 A1 | 11/2012 | Douglas et al. | |
| 2012/0289895 A1 | 11/2012 | Tsoukalis | |
| 2013/0138061 A1 | 5/2013 | Yamane | |
| 2013/0180876 A1 | 7/2013 | Pidgeon et al. | |
| 2013/0213891 A1 | 8/2013 | Karoor | |
| 2013/0267920 A1 | 10/2013 | Nicolini | |
| 2013/0274773 A1 | 10/2013 | Shturman et al. | |
| 2013/0331805 A1 | 12/2013 | Brennan | |
| 2013/0331823 A1 * | 12/2013 | Askem | F04B 45/047 604/543 |
| 2014/0034638 A1 * | 2/2014 | Whelan | B60K 15/04 220/86.2 |

* cited by examiner

ASPIRATION SYSTEM FOR THROMBECTOMY PROCEDURES

This application is a continuation of Ser. No. 14/550,941, filed Nov. 22, 2014, which claims priority from provisional patent application Ser. No. 61/916,034, filed Dec. 13, 2013. The entire contents of each of these applications are incorporated herein by reference.

BACKGROUND

Technical Field

This application relates to an aspiration pump and more particularly to an aspiration pump for use in thrombectomy or other vascular procedures.

Background of Related Art

There have been various attempts to break up clots and other obstructing material in grafts or native vessels. One approach is through injection of thrombolytic agents such as urokinase or streptokinase. These agents, however, are expensive, require lengthy hospital procedures and create risks of drug toxicity and bleeding complications as the clots are broken.

Other approaches to breaking up clots involve mechanical thrombectomy devices. For example, U.S. Pat. No. 5,766,191 discloses a cage or basket composed of six memory wires that expand to press against the inner lumen to conform to the size and shape of the lumen.

U.S. Pat. No. 6,090,118, incorporated herein by reference in its entirety, discloses a wire rotated to create a standing wave to break-up or macerate thrombus. The single wire is less traumatic than the aforedescribed basket device since it minimizes contact with the graft wall while still effectively mechanically removing thrombotic material.

U.S. Pat. Nos. 7,037,316 and 7,819,887, both incorporated herein by reference in their entirety, disclose another example of rotational thrombectomy wires for breaking up clots in grafts. The thrombectomy wire has a sinuous shape at its distal end and is contained within a sheath in a substantially straight non-deployed position. When the sheath is retracted, the distal portion of the wire is exposed to enable the wire to return to its non-linear sinuous configuration. Actuation of the motor causes rotational movement of the wire, creating a wave pattern, to macerate thrombus.

In neurovascular thrombectomy procedures, the thrombectomy wire needs to navigate tortuous vessels. That is, the wire is inserted through femoral artery and then must navigate small and tortuous vessels as it is advanced to the smaller cerebral arteries of the brain. Within the brain, the carotid and vertebrobasilar arteries meet to form the circle of Willis. From this circle, other arteries, e.g., the anterior cerebral artery, the middle cerebral artery and the posterior cerebral artery, arise and travel to various parts of the brain. Clots formed in these cerebral arteries can cause stroke and in certain instances death of the patient.

Due to the size and curves of the vessels en route to the cerebral arteries from the femoral artery, as well as the size and structure of cerebral arteries themselves, access is difficult. If the thrombectomy device is too large then navigation through the small vessels, which can be as small as 1 mm, would be difficult. Also, if the device is too stiff, then it can damage the vessel walls during insertion. On the other hand, if the device is too flexible, it will lack sufficient rigidity to be advanced around the vessel curves and can be caught in the vessel. The devices disclosed in U.S. Pat. Nos. 8,764,779 and 8,663,259, the entire contents of which are incorporated herein by reference, provide a thrombectomy device for breaking cerebral clots that strikes the optimal balance of flexibility and stiffness, thus effectively having the insertability of a tracking guidewire while enabling high speed rotation to effectively macerate clots without damaging vessels.

After particles have been macerated, especially in neurovascular thrombectomy procedures, it would be advantageous to aspirate the macerated particles to ensure the particles do not travel downstream, which if sufficiently large could result in stroke or even death.

SUMMARY

The present invention advantageously provides in one aspect an aspiration system comprising a housing containing an aspiration pump and a chamber, a collection bag in fluid communication with the chamber, and a tubing assembly including a first tube portion connected to the chamber. The tubing assembly has a connector to split the first tube portion into a second and third tube portion, the second tube portion is in fluid communication with a first catheter to aspirate particles through the first catheter and the third tube portion is in fluid communication with a second catheter to aspirate particles through the second catheter.

In some embodiments, the connector comprises a T-fitting connected to an input end of the first tube portion and communicating with an output end of the second tube portion and an output end of the third tube portion.

In some embodiments, the chamber has an input port to receive particles and an output port to transport aspirated particles from the chamber into the collection bag.

In some embodiments, the collection bag is shipped in a substantially flattened position underneath a base of the housing.

The aspiration pump can include a switch electrically connected to the pump to turn the pump on and off. An indicator can be included to provide an indication to the user that the collection bag is full.

In some embodiments, when backpressure in the collection bag exceeds a predetermined amount, the controller will transmit a signal to the pump to shut off the pump.

In some embodiments, a non-conductive shipping tab is removable to complete a circuit to enable actuation of the pump.

In some embodiments, a substantial portion of the first tube portion is positioned underneath a base of the housing during shipping. During shipping, the collection bag can be positioned underneath a portion of the first tube portion.

In some embodiments, a first valve is connected with the second tube portion and a second valve is connected with the third tube portion, the first and second valves selectively actuable to enable fluid flow through the respective tube.

In another aspect of the present invention, an aspiration system is provided comprising a housing containing an aspiration pump and a chamber, the housing having a top portion and a base. In a shipping configuration, a tubing assembly has a first tube wrapped in a wound configuration, at least a substantial portion of the first tube positioned underneath the base. A collection bag is in fluid communication with the housing and in the shipping configuration at least a portion of the collection bag is positioned underneath the substantial portion of the first tube.

In some embodiments, the tubing assembly includes a second tube and a third tube, each in fluid communication with the first tube. In some embodiments, the first tube has a split connector to separately connect with the second and third tubes. The aspiration pump can further include a first valve connected with the second tube and a second valve connected with the third tube, the first and second valves selectively actuable to enable fluid flow through the respective tube. The system can further include a power pack positioned within the housing.

In some embodiments, the chamber has an input port to receive aspirated particles and an output port to transport aspirated particles from the chamber into the collection bag.

The present invention also provides in another aspect a disposable sterile aspiration kit comprising a pump, a power pack for powering the pump, a tubing assembly for transporting aspirated particles from the body, and a collection bag for receiving aspirated particles, wherein the pump aspirates the particles through the tubing and pumps the aspirated particles into the collection bag. In preferred embodiments, pump and the power pack are positioned in a housing. In some embodiments, the tubing is positioned underneath the housing. In some embodiments, the housing includes a chamber, the pump activated to aspirate the particles into the chamber in the housing and to pump the aspirated particles from the chamber through the tubing assembly into the collection bag.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1:
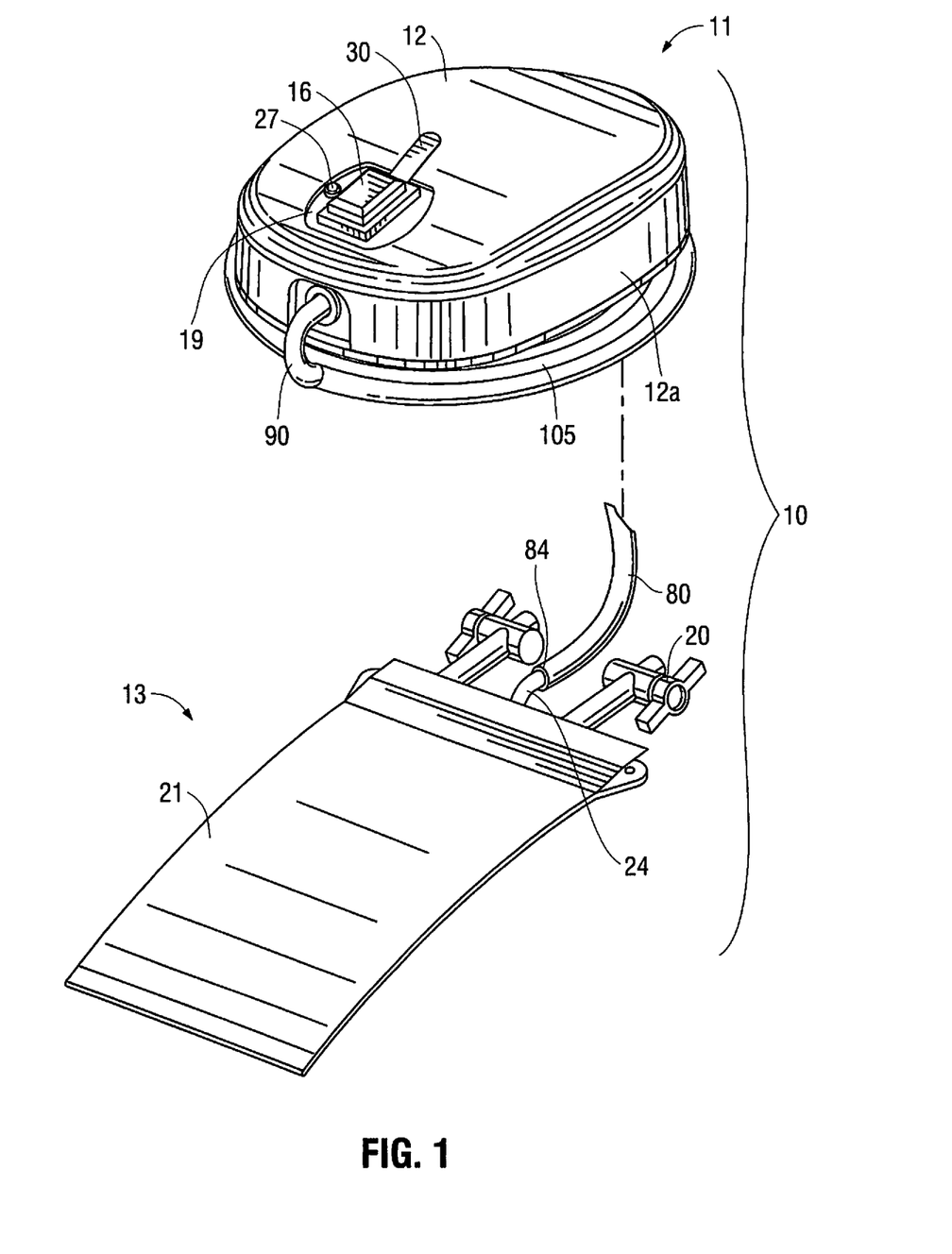
FIG. 1 is a perspective view of the aspiration system of the present invention.

Referring now in detail to the drawings where like reference numerals identify similar or like components throughout the several views, FIG. 1 illustrates the pump housing 11 and collection bag assembly 13 of the aspiration system 10 of the present invention, which are separated for clarity. The system 10 is designed for use with a thrombectomy apparatus, such as the thrombectomy apparatus 200 described in detail below. The system 10 can also be utilized for aspiration in conjunction with other thrombectomy devices as well as in other medical procedures requiring aspiration.

Figure 3:
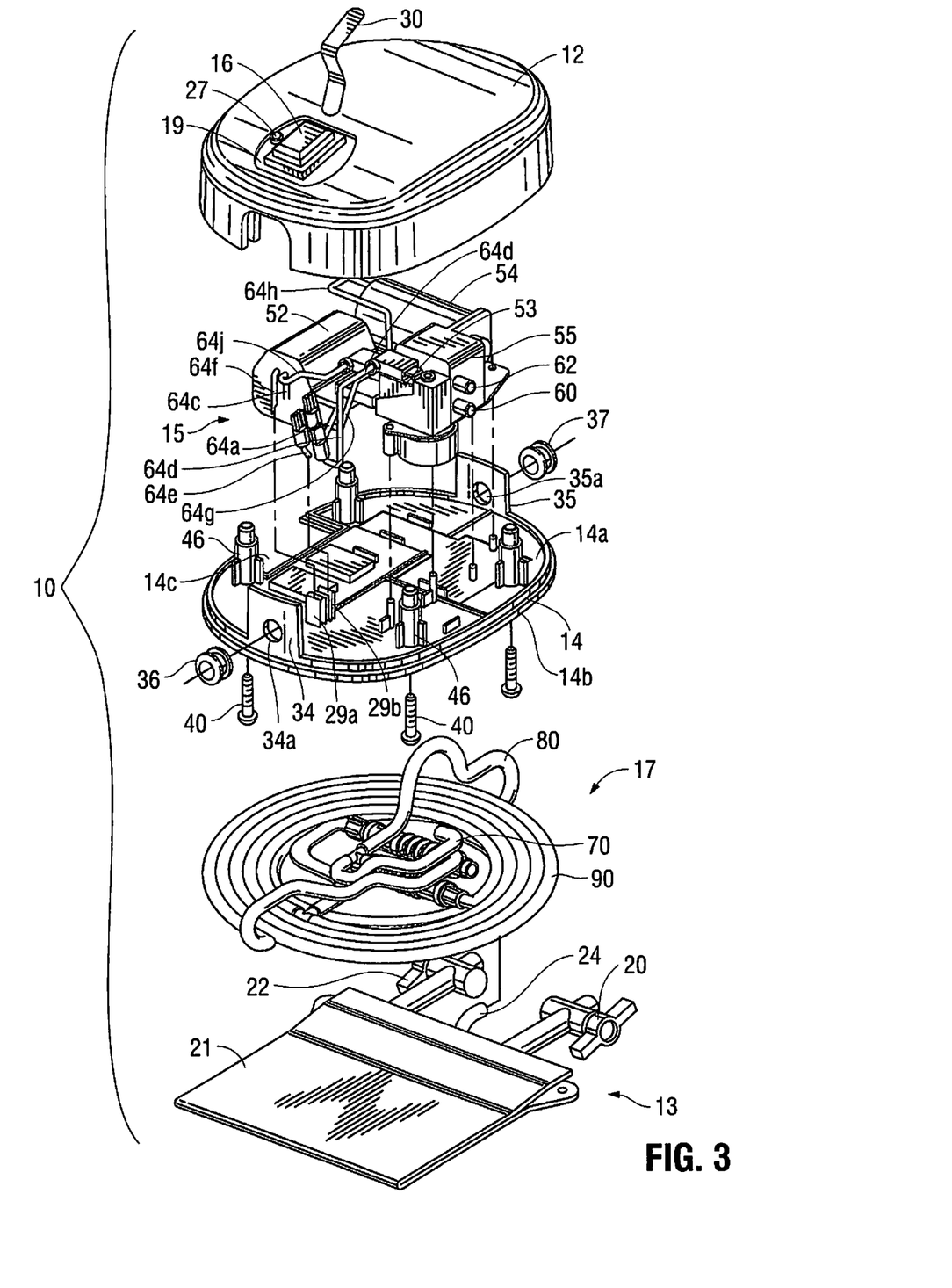
FIG. 3 is an exploded view of the aspiration system of FIG. 1.

Turning initially to FIGS. 1 and 3, pump housing 11 includes a top housing or cover 12 and a pump base 14. Contained within the pump housing 11 is an electrical subassembly 15 which includes an on/off power switch 16 protruding through opening 19 in top cover 12. The pump switch 16 can include a light to indicate when the switch is on to operate the pump to aspirate particles from the surgical site. Other types of indicators are also contemplated, including audible indicators. The components of the electrical subassembly are discussed in more detail below. Aspiration system 10 also includes a tubing assembly 17 having bag tubing 80 and pump tubing 90, both described in detail below. Collection bag assembly 13 of system 10 includes a bag 21, shown in the flattened (unfilled) shipping position in FIGS. 1 and 3, and a connector 24 for bag tubing 80. The collection bag 21 is preferably shipped positioned underneath the base 14 and tubing assembly 17 to provide a compact unit to facilitate shipping and portability. Collection bag assembly 18 further includes a one way stopcock 20 to drain the collection bag 21 if desired by opening the valve. A second stopcock 22 can also be provided for collection bag drainage. An LED indicator 27, visible through top cover 12, provides an indicator when the collection bag 21 is full.

Figure 5:
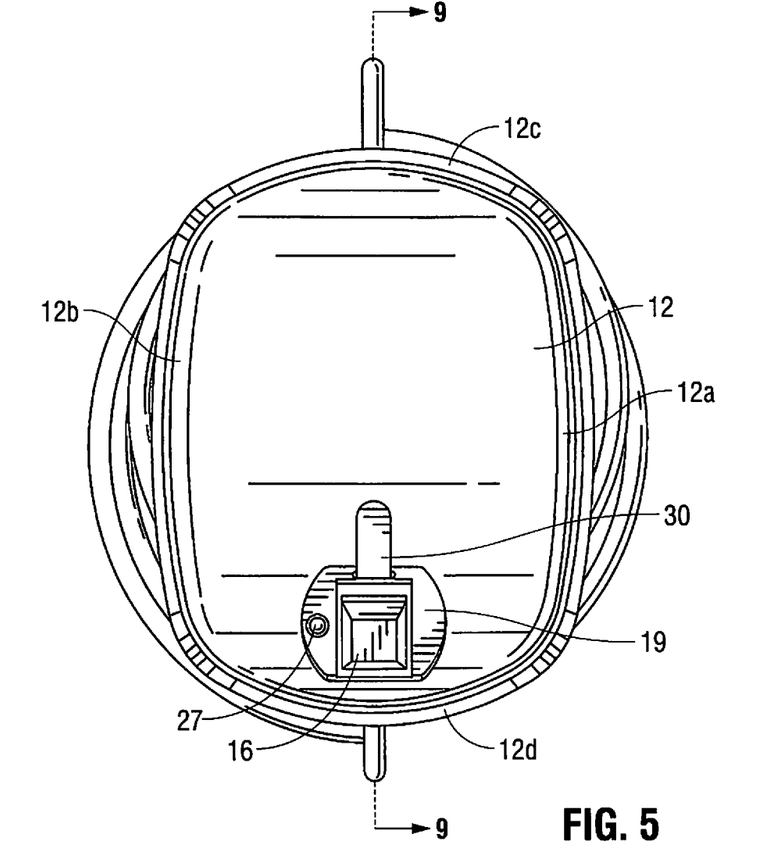
FIG. 5 is a top view of the aspiration system of FIG. 1.
Figures 9, 10:
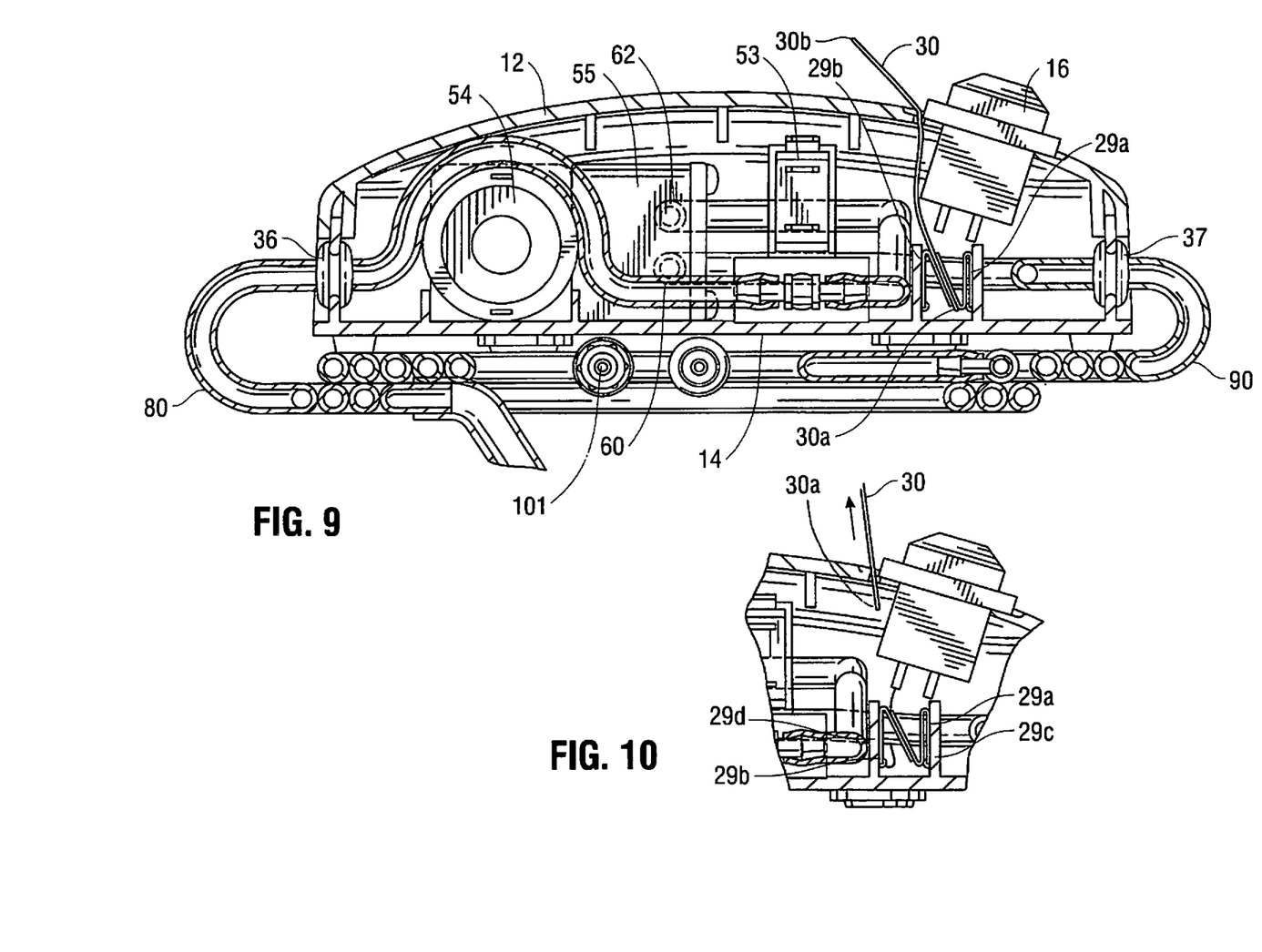
FIG. 9 is a cross-sectional view of the aspiration system taken along line 9-9 of FIG. 5.
FIG. 10 is a cross-sectional view illustrating removal of the shipping tab.
Figure 11:
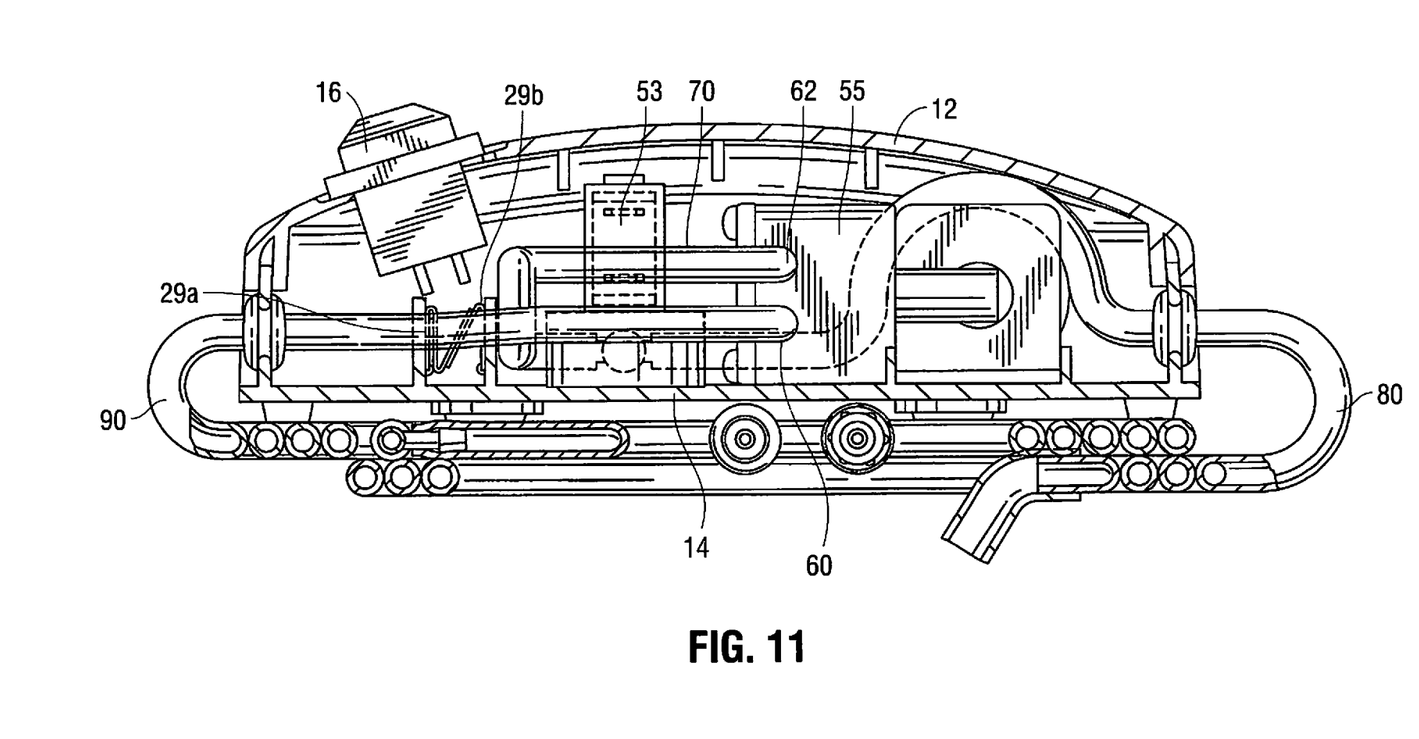
FIG. 11 is a cross-sectional view of the aspiration system of FIG. 1 from the opposite side of FIG. 9.

Top cover 12, as shown in FIGS. 1 and 5, has substantially linear sides 12a and 12b and curved ends 12c and 12d. Top cover 12 also has an opening 19 for the on/off switch 16. A non-conductive pull tab 30 extends though the opening 19 and breaks the circuit during shipping to prevent inadvertent actuation of the pump 10. This is best seen by comparing FIGS. 9 and 10, wherein the distal end 30a of pull tab 30 is interposed between conductive plates 29a, 29b, positioned between respective posts 29c, 29d, and the proximal end 30b extends outside the pump housing 11 through opening 19 so it is accessible to the user. When desired to operate the pump 10, the pull tab 30 is moved in the direction of the arrow of FIG. 10, thereby allowing plates 29a, 29b to come into electrical contact to complete the circuit described below.

Figure 6:
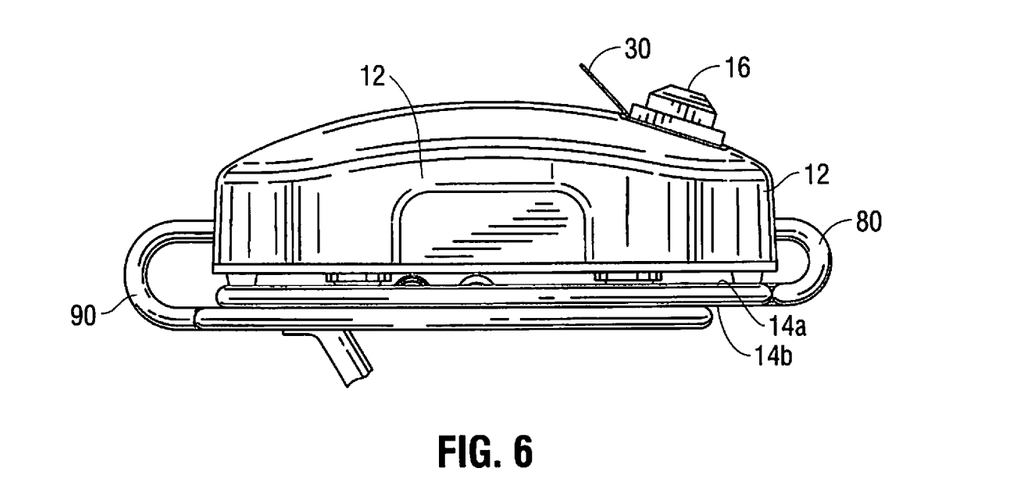
FIG. 6 is a side view of the aspiration system of FIG. 1.

Base 14 has a top surface 14a and a bottom surface 14b (see e.g., FIGS. 3 and 6). Bottom surface 14b is designed to rest on the table. Screws 40 extend through cylindrical posts 46, not all of which are labeled for clarity, to attach the top cover 12. Pads (not shown) can be provided on the screw heads to provide a smoother surface. Base 14 also includes a cutout 14c.

Figure 4:
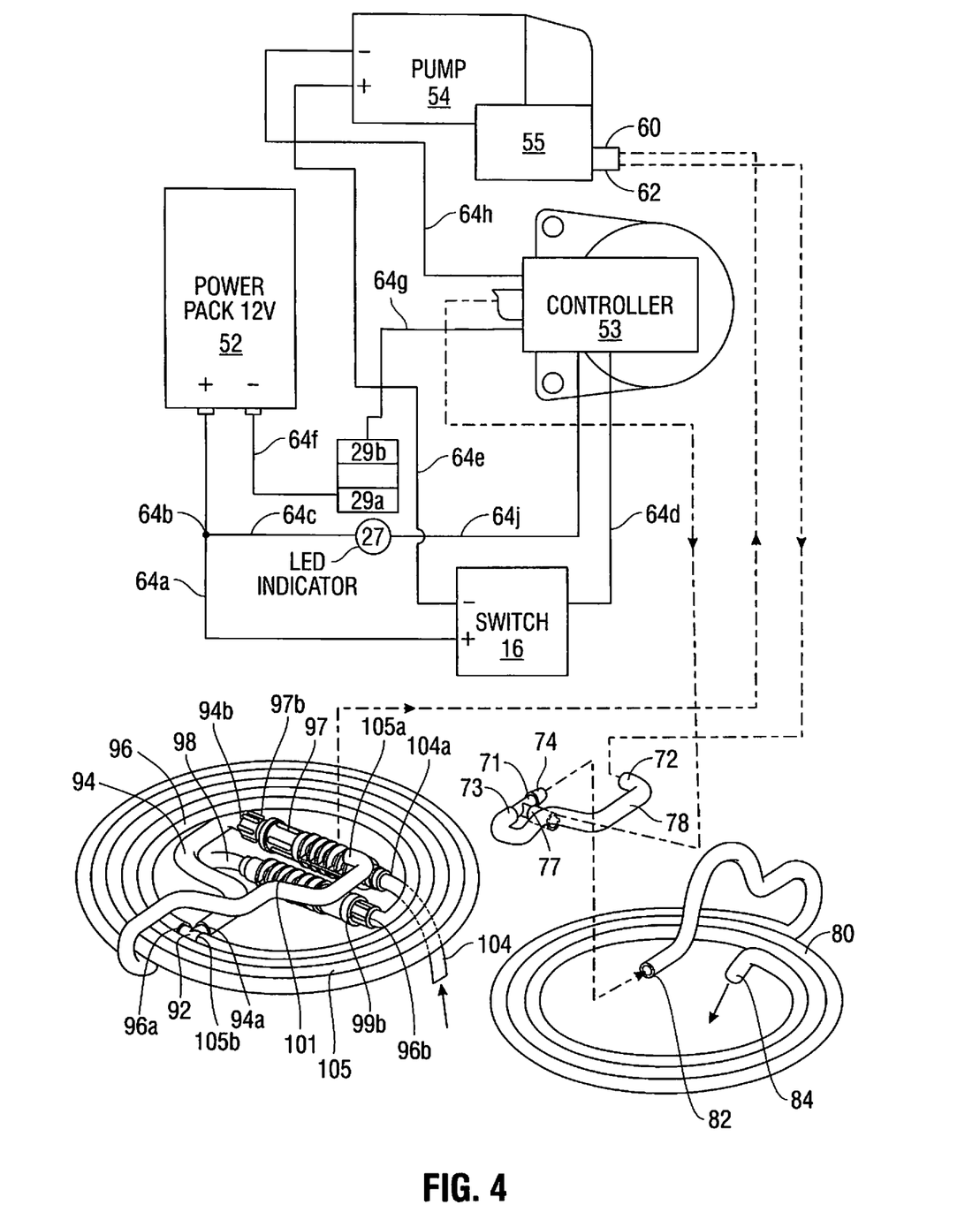
FIG. 4 is a perspective view of the tubings and a diagrammatic view of the pump wiring and tubing connections.

The electrical subassembly 15, best shown in FIGS. 3 and 4, includes a controller 53 and a motor pump 54. An output port 62 and an input port 60 extends from housing (chamber) 55. A power pack 52 containing one or more batteries e.g., 12 volt batteries, is mounted on base 14. Blood and particles are suctioned via input port 60 into the chamber by the pump 54 and outputted by the pump 54 through output port 62 into the collection bag 21.

Turning now to the tubing assembly 17, and with reference to FIGS. 3 and 4, tubing assembly 17 includes bag tubing 80, pump tubing 90 and connector tube 70. Bag tubing 80 has a tube inlet end 82 which connects to T-connector 71 of connector tube 70 at connection port 74. Tube outlet end 84 of bag tubing 80 connects to the connector 24

(FIG. 3) of the collection bag assembly 13 to transport particles from bag tubing 80 into the bag 21.

T-connector 71 is connected to output end 73 of connector tube 70. As noted above, port 74 of T-connector 71 receives inlet end 82 of bag tubing 80. The other port (the 90 degree port) of T-connector 71 receives connector 77 which is connected to the controller 53. In this manner, when the bag 21 is full and backpressure is detected by the controller 53, the controller 53 sends a signal to the pump 54 to turn off the pump 54 so that suction is terminated and the bag 21 is not overfilled which could result in the bursting of the bag 21. The opposing end 72 of connector tube 70 connects to the output port 62 of the chamber 55 (housing). In this manner, the blood or other particles are transported from chamber 55 through end 72 into connector tube 70, out through connection port 74, into inlet end 82, through bag tubing 80, out outlet end 84, into connector 24 and into collection bag 21.

Pump tubing 90 includes a long tube 105, a connector tube 96 and short tube 94. T-connector 92 splits the fluid communication of long tube 105 into connector tube 94 and short tube 96 so that one tube connects to the guide catheter and the other tube connects to the thrombectomy catheter as described below. Tube 105 has one end 105a which connects to the input port 60 of the chamber 55 for application of suction. The tube 105 extends in a series of circular adjacent wraps. The opposing end 105b connects to tubes 94, 96 via T-connector. More specifically, T-connector 92 joins the input end 105b of long tube 105 to output end 94a of short tube 94 via its 90 degree port. The opposing input end 94b of short tube 94 connects to luer 97b of switch valve 97, with the output end 104a of catheter tubing 104 connected to the input end of the switch valve 97. Tube 94 extends in a somewhat partial S-shape as shown. Thus, short tube 94 fluidly joins catheter tubing 104 to long tube 105 as particles and blood from the thrombectomy catheter are aspirated through the lumen in the catheter into tubing 104, out end 104a into the lumen of valve 97, out valve 97 and into input end 94b of short tube 94, out output end 94a of short tube 94, into input end 105b of long tube 105, and out end 105a of long tube 105 into the chamber (housing) 55 as end 105a is connected to inlet port 60 of housing 55. In an alternate embodiment, the switch valve 97 can be connected directly to the side port of the RHV, as shown for example in FIG. 2A.

The T-connector 92 also connects long tube 105 to connector tube 96 at output end 96a at its 180 degree port. The opposing end 96b of connector tube 96 extends into luer 99b of the switch valve 101. Short tube 96 extends in a circular fashion around an arc of about 270 degrees. Tubing 98 at the input end of the valve 101 is connected to the guide catheter. Thus, particles and blood are aspirated through the lumen of the guide catheter into catheter tubing 98, through the lumen in the switch valve 101, out the opposing end of switch valve 101, into input end 96b of short tube 96, out output end 96a of short tube 96, into input end 105b of long tube 105, through long tube 105 and out end 105a of long tube 105, into input port 60 and into the chamber (housing) 55. In an alternate embodiment, the switch valve 101 can be connected directly to the side port of the RHV, as shown for example in FIG. 2A.

Figures 7, 8:
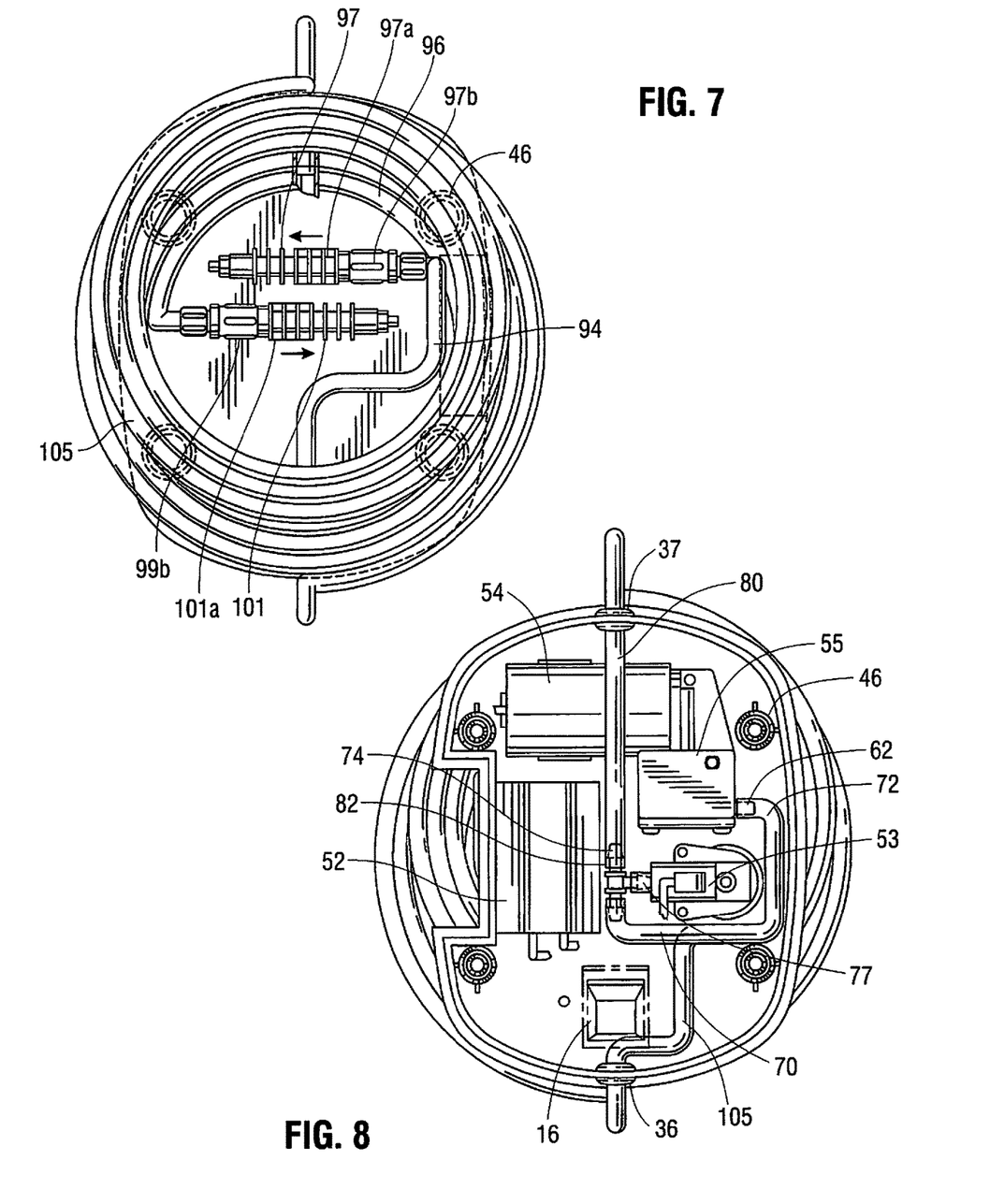
FIG. 7 is a top view showing the tubing of the aspiration system of FIG. 1.
FIG. 8 is a top view of the aspiration system, with the top half of the pump housing removed to illustrate internal components.

The switch valve 97 can be selectively actuated to enable suction through the thrombectomy catheter described below and the switch valve 101 can be selectively actuated to enable suction through the guide catheter, also described below. In one embodiment, the switch valves 97, 101 each have a slider mechanism 97a 101a, respectively, (see FIG. 7) which when slid in one direction clamps down on the respective tube (which forms the lumen in the switch valve for fluid/particle flow) to close off flow and when slid in the other direction unclamps the tube to enable suction. In FIG. 7, the slider mechanisms 97a, 101a are shown in the open position. When moved in the direction of the arrow, they are moved to a closed position to close off flow. Other types of valves and mechanisms to open and close off flow are also contemplated. Luer locks 97b, 99b, provide the connection of tubes 94, 96 to the respective valve 97, 101.

The diagram of FIG. 4 illustrates the electrical connections of the components. Switch 16 is connected to the positive terminal of the power pack 52 via wire 64a. Wire 64A splits at junction 64b so that wire 64c connects the power pack 52 to the LED indicator 27. The LED indicator 27 is connected to controller 54 via wire 64j. Switch 16 is also connected to controller 53 via wire 64d which provides an input signal to the controller 53 when the switch 16 is turned on. Switch 16 is further wired to the pump 54 via wire 64e. The negative terminal of the power pack 52 is connected via wire 64f to the conductive plate 29a. The opposing conductive plate 29b is connected to the controller via wire 64g. The controller 53 and pump 54 are connected via wire 64h. As noted above, non-conductive tab 30 is seated between plates 29a, 29b to break the circuit.

When the collection bag 18 becomes full, it is sensed by the controller 53 and the pump 54 is automatically turned off. More specifically, the controller 53 measures back pressure in the collection bag 21. As the bag 21 becomes fuller, it is more difficult to fill because it will not be expanded. When the back pressure rises to a predetermined amount, the controller 53 will transmit a signal to the pump 54 to shut off the pump 54. In this way, over expansion and potential bursting of the collection bag 21 is prevented.

The pump 54 in one embodiment includes a piston actuated by a motor. When the piston moves in a first direction, e.g., outwardly with respect to the chamber 55, blood and particles are suctioned through pump tubing 90, and when the piston moves in the reverse direction, e.g., into the chamber 55, the blood and particles are pumped from the chamber 55 into the bag tubing 80 and into the collection bag 21.

The aspiration system of the present invention can be provided in a portable kit. In this manner, the entire assembly (pump housing, tubing and collection bag) can be provided in a sterile package. Additionally, the entire assembly (pump housing, tubing and collection bag) in some embodiments can be disposable.

Figure 2A:
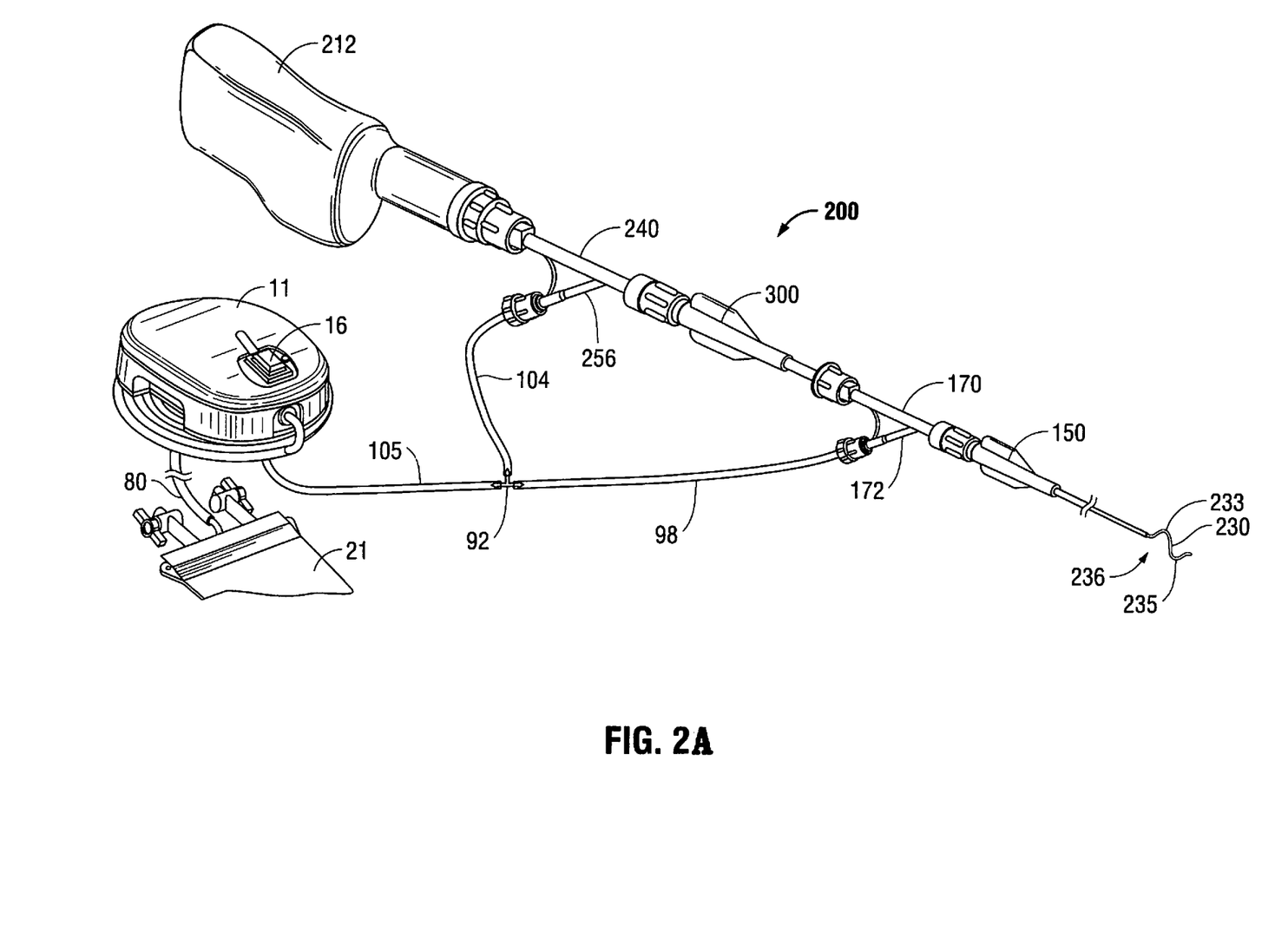
FIG. 2A is a perspective view of the aspiration system of FIG. 1 shown attached to a thrombectomy apparatus.
Figure 2B:
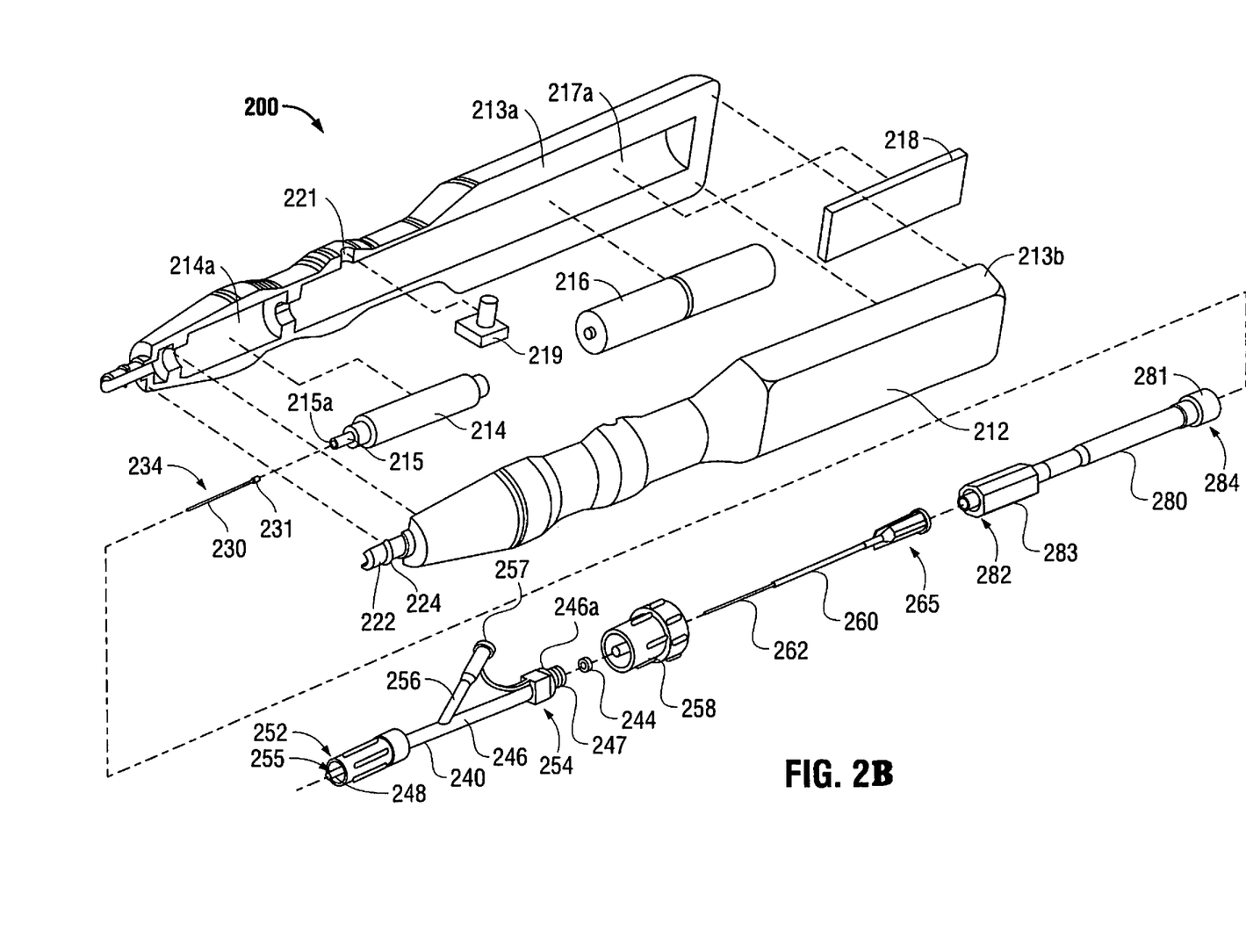
FIG. 2B is an exploded view of the proximal portion of the thrombectomy apparatus of FIG. 2.

The pump of the present invention will can be used with a variety of devices to aspirate blood and/or particles. By way of example, it will be now be described in conjunction with the thrombectomy apparatus described in U.S. Pat. No. 8,764,779. Further details of the device of the U.S. Pat. No. 8,764,779 can be understood from the patent, the entire contents of which are incorporated herein by reference. The thrombectomy apparatus is shown in FIGS. 2A and 2B and is designated generally by reference numeral 200. The apparatus includes a motor housing 212, a rotational thrombectomy wire 230, a rotating hemostatic valve (RHV) 240, an introducer sheath 260 and a telescoping tube or tubular connector 280. The RHV 240 is connectable to an introducer catheter 300 discussed below in conjunction with the method of use (see e.g. FIG. 2C). The introducer sheath 260 is insertable into the RHV 240 to facilitate insertion of the thrombectomy wire 230 through the RHV 240 and introducer catheter 300.

The thrombectomy apparatus or assembly 200 provides a rotational thrombectomy wire as a separate unit from a catheter. That is, the thrombectomy wire 230 is provided as a separate unit insertable through the RHV 240. The RHV 240 has a distal end 252 connected to a proximal end of the introducer catheter 300 (see FIG. 2C) to access the surgical site. The introducer sheath 260 aids insertion of the thrombectomy wire into the RHV 240 and through the introducer catheter 300, with the walls of the introducer sheath 260 maintaining the non-linear distal end of the wire 230 in a substantially straightened (substantially linear) configuration as it enters the RHV 240.

Additionally, the thrombectomy wire 230 of the present invention can be slid within the introducer sheath 260 and introducer catheter 300 prior to connection to the motor, if desired. This can aid introduction and manipulation of the wire 30 since it is less cumbersome and of lighter weight than if the motor housing was attached during manipulation of the wire. However, it is also contemplated that the wire 230 could be attached to the motor housing 212 prior to insertion through the introducer sheath 260, RHV 240 and the introducer catheter 300 and thus the wire 230 would be slidable within the introducer sheath 260 (and introducer catheter 300) with the motor housing 212 attached. Thus, the motor housing 212 can be attached to the wire at a desired time prior to or during the procedure.

The motor housing 212, which also forms a handle portion, contains a motor and motor drive shaft extending therefrom. A gear reducer (not shown) could optionally be provided to reduce by way of example the rotational speed of the motor 252 from 15,000 rpm to 1500 rpm, 750 rpm, 150 rpm, etc. One or more batteries, such as a 3 Volt battery, is positioned in the housing 212 for powering the motor 214. The motor drive shaft 215 connects at end 215a to a proximal end of the thrombectomy wire 230 by various couplings, such as for example a snap fit wherein cap 231 of at the proximal end of wire 30 is frictionally fit over the motor drive shaft 15. Various other types of connections are also contemplated such as magnetic couplers. A printed circuit board can also be provided within the housing 230 and is designated by reference numeral 218.

Switch 219 extends though recess 221 in housing half 213a and in a corresponding recess in housing half 213b. A potentiometer (not shown) can optionally be wired to the motor to enable dialing the motor speed up or down to adjust the rotational speed of the thrombectomy wire 230 to adjust for various procedures and/or clot locations and sizes. In a preferred embodiment, the potentiometer is used as a two terminal variable resistor, i.e. a rheostat, by not connecting the third terminal. In this manner, in the initial position, the motor speed is at the desired minimum and rotation of a knob (or in alternate embodiments sliding of a knob) progressively increases the motor speed. Thus, the on/off switch 219 extending from the housing 212 is electrically connected to the motor 215 to turn on the motor 215 to activate the apparatus, i.e. rotate the wire 230.

Figure 2C:
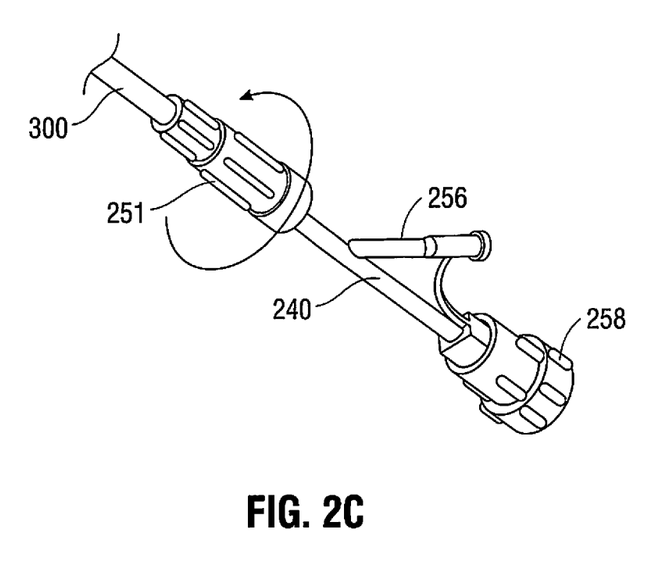
FIG. 2C is a perspective view illustrating attachment of the RHV to the introducer catheter.

Turning to the other components illustrated in FIGS. 2-4, rotating hemostatic valve (RHV) or housing 240 as noted above is connectable to an introducer catheter 300 (see FIG. 2C). A conventional introducer catheter can be utilized or alternatively a specially designed catheter for use with the apparatus of the present invention can be utilized. As is standard, the RHV 240 is rotatable with respect to the catheter 300 to alter the orientation of the side arm 256.

Side arm 256 extends from the tubular portion 246 of RHV 240 and has a port 257 for introduction of fluids and/or application of vacuum as described below. Luer lock is provided at the distal end 255 of RHV 240 to connect to the introducer catheter 300 as internal threads of rotation knob 252 threadingly engage external proximal threads of the introducer catheter 300. Tube extension 248 fits within the lumen of the introducer catheter 300 when attached.

Tubular portion 246 of RHV 240 includes a lumen extending therethrough to slidably receive the tubular portion 262 of the introducer sheath 260. Proximal cap 258 at proximal end 254 has internal threads to threadingly attach to external proximal threads 247 of RHV 240 for attachment of the cap 258 to the RHV 240. Thus, as cap 258 is tightened on RHV 240 by rotation, it compresses rings against the tubular portion 262 of introducer sheath 260 extending therethrough to connect the introducer sheath 260 to the RHV 240. A proximal seal can also be provided.

Side arm 256 of RHV 240 has a lumen in fluid communication with the lumen of tubular portion 46. Fluids such as imaging dye can be injected through the arm 256, flowing through the lumens, i.e., through the space between the inner wall of the lumen of the tubular portion 246 and the outer wall of the introducer sheath 260, and then through the space between the thrombectomy wire 230 and the inner wall of the introducer catheter 300, exiting a distal opening 303 (FIG. 2D) in the introducer catheter 300 to flow into the vessel. This imaging dye can be used to provide an indication that fluid flow has resumed in the vessel.

The side arm 256 is also used for vacuum to suction particles detached from the vessel by the rotational wire 230. The aspirated particles flow into the distal opening 303 (FIG. 2D) of the introducer catheter 300 and through the space between the wire 230 and the inner wall of the introducer catheter 300, continuing through the lumen in the tubular portion 246 lumen 255 and then exiting through the outlet 257 into catheter tubing 104 of the system 10, through long tube 105, into the chamber 55 and outputted via tubes 70 and 80 into the collection bag 18.

Figure 2D:
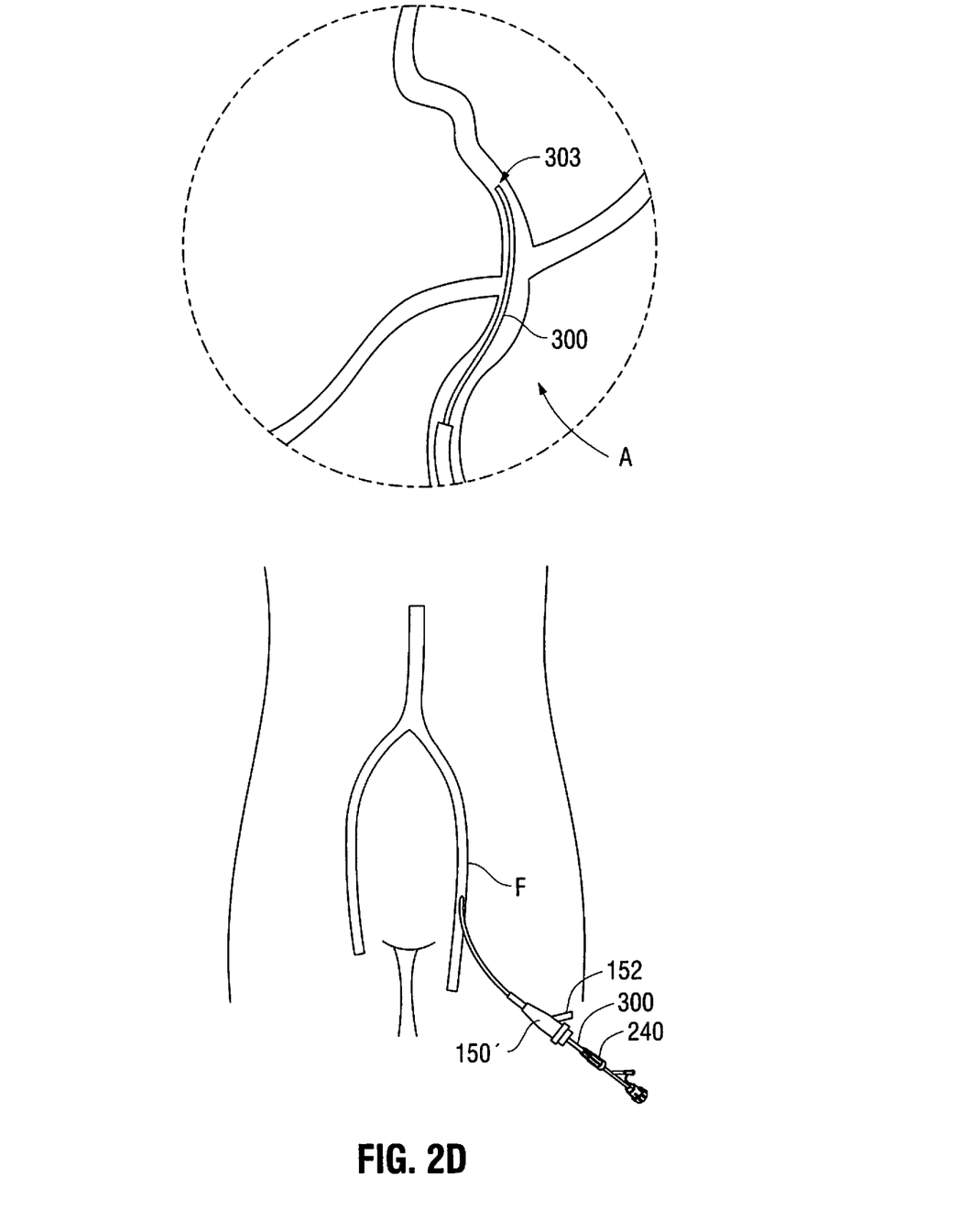
FIG. 2D illustrates insertion of the introducer catheter of the thrombectomy apparatus through a guide catheter and into the circle of Willis and insertion and attachment of the RHV to the introducer catheter.

It should also be appreciated that the guide catheter 150 discussed in conjunction with the method of use below can also have a side arm 152 for injection of fluid (see FIG. 2D). The side arm 152 is also used for aspiration by system 10. Alternatively, a RHV 170 with a side arm 172 can be used with a guide catheter 150 (which does not have a side arm) as shown in FIG. 2A. Actuation of the pump aspirates particles through the space between the introducer catheter 300 and guide catheter 150, into tubing 98 and long tube 105 and into the chamber 55 where it is outputted via tubes 70 and 80 into the collection bag 18.

In the alternate embodiment, the RHV does not have a side arm. In this embodiment, a guide catheter with a side arm can be used for injection and suction. However, the guide catheter with a side arm can also be used in conjunction with an RHV with a side arm so that suction can occur through the RHV and neuro catheter and/or through the guide catheter. This is shown in FIG. 2D.

The tubular portion 262 of introducer sheath 260, as noted above, extends through the lumen of RHV 240 and terminates either within RHV 240 or at a proximal portion of the lumen of the introducer catheter 300. The tubular portion 262 preferably has a stiffness greater than the stiffness of the thrombectomy wire 230 to maintain the wire 230 in a straightened position during passage of wire 230 into the RHV 240 for subsequent passage through the lumen of the introducer catheter 300 to the surgical site.

Proximal end 265 of introducer sheath 260 is attachable to connector tube 280. Preferably, the enlarged proximal end 265 has a threaded flange to threadingly engage the internal threads on the tubular connector 280. A valve can be provided within the distal end 282 of the connector tube 280 in addition or instead of a valve in a proximal end 265 of the introducer sheath 260 to seal escape of fluid to improve the vacuum through the side arm 256.

Note the tube 280 and introducer sheath 260 can alternatively be provided as one unit, attached together and positioned over the thrombectomy wire 230 as an attached unit. However, in alternative embodiments, the wire 230 is inserted through the introducer sheath 260 and manipulated through the introducer catheter 300 to the surgical site. Once positioned, the connector tube 280 is then threadingly attached at the distal end 282 to the introducer sheath 260 as noted above and at a proximal end 284 to the motor housing 212. In this version, the connector tube 280 can be positioned over the wire 230 prior to insertion of the wire 230 through introducer sheath 260 or after insertion through the sheath 260. The wire 230 can be packaged with the sheath 260 and the tube 280 positioned thereover, or packaged apart from the sheath 260 and tube 280.

Proximal end 284 of connector tube 280 is configured for attachment to the motor housing 212. A ring is seated within an internal groove of connector tube 280 to provide a snap fit. As noted above, proximal end of the wire 230 is attached to the drive shaft 215 of the motor 214. In one embodiment, end cap 231 of wire 230 is snap fit within opening 215a in motor shaft 215. Other ways to attach the wire 230 and motor shaft 215 are also contemplated such as a bayonet mount for example or a magnetic coupler wherein a magnet is attached to wire 230 and mates with a magnet attached to the motor housing.

As can be appreciated, by having a detachable motor housing 212, different handles with different motor speeds and/or different batteries can be utilized by attachment to the wire 230. This can even be achieved during the same surgical procedure.

In some embodiments, the housing can be detached, sterilized and reused after recharging of the battery or replacing the battery.

In some embodiments, as an alternative to direct connection to the motor shaft, the proximal end of wire 230, after insertion to the surgical site or prior to insertion, can be attached at a proximal end to a coupler tube which is connected to a gear reducer. The connection can be a friction fit, a magnetic coupling or a twist connect, e.g., a bayonet connection, by way of example.

The wire 230 has a distal coiled tip angled with respect to the longitudinal axis. FIG. 2A shows the wire forming a sinuous shape. In an alternative embodiment, the wire forms a J-tip which creates a standing wave upon rotation. In the J-tip configuration, due to the angle, when the wire is rotated by the motor at sufficient speed at least one vibrational node is formed. Details of this creation of a standing wave are described in U.S. Pat. No. 6,090,118, the entire contents of which are incorporated herein by reference.

The wire 230 forms a substantially sinuous shape, resembling a sine curve. More specifically, wire 230 has a substantially linear portion extending through most of its length, from a proximal region, through an intermediate region, to a distal region. At the distal region 236, wire 230 has a sinuous shape in that as shown it has a first arcuate region 233 facing a first direction (upwardly as viewed in the orientation of FIG. 2A) and a second arcuate region 235, spaced longitudinally from the first arcuate region 233, facing a second opposite direction (downwardly as viewed in the orientation of FIG. 2A). These arcuate regions 233, 235 form "peaks" to contact vascular structure as the wire 230 rotates. This angled (non-linear) distal portion of wire 230 can include a coiled portion with a covering material to block the interstices of the coil. Note in a preferred embodiment, the amplitude of the proximal wave (at region 233) is smaller than the amplitude of the distal wave (at region 235), facilitating movement in and out of the catheter.

When the wire 230 is fully retracted within the introducer catheter 300, the curved regions of the wire 230 are compressed so the distal region is contained in a substantially straight or substantially linear non-deployed configuration. When the introducer catheter 300 (attached to RHV 240) is retracted by proximal axial movement, or the wire 230 is advanced with respect to the introducer catheter 300, or the wire 230 and catheter 300 are both moved in the respective distal and proximal directions, the distal region of the wire 230 is exposed to enable the wire 230 to return to its non-linear substantially sinuous configuration for rotation about its longitudinal axis within the lumen of the vessel.

Thus, as can be appreciated, the wire 230 is advanced within the introducer catheter 300 which is attached at its proximal end to the distal end of the RHV 240. When at the desired site, the wire 230 and introducer catheter 300 are relatively moved to expose the wire 230 to assume its non-linear shape for motorized rotational movement to break up thrombotic material on the vessel wall. If a J-tip wire is utilized, the wire can be rotated within the introducer catheter 300 to re-orient the wire.

The flexible tubular portion 262 of the introducer sheath 300 can optionally contain one or more braided wires embedded in the wall to increase the stiffness. Such braided wires would preferably extend the length of the sheath 300.

In an embodiment of the coiled tip being composed of shape memory material, the memorized configuration is sinuous or s-shape as in FIG. 2A. In the state within the introducer catheter 300, the wire is in a substantially linear configuration. This state is used for delivering the wire to the surgical site. When the wire is exposed to warmer body temperature, the tip transforms to its austenitic state, assuming the s-shaped memorized configuration. Alternatively, the coiled tip of the wire can be compressed within the wall of the introducer catheter and when released, assumes its shape memorized non-linear shape. The coiled tip can alternatively be a radiopaque coil/polymer pre-shaped to an "S".

Details of the wire 230 are described in U.S. Pat. No. 8,764,779, previously incorporated by reference in its entirety herein.

The use of the thrombectomy apparatus 10 will now be described. The use, by way of example is shown and described with respect to the embodiment of FIG. 2A with the sinuous tip wire, it being understood that other wires can be utilized in a similar manner.

An access sheath (not shown) is inserted into the vessel and then a guidewire e.g. 0.035 or 0.038 inches in diameter, and a guide catheter 150' are inserted through the sheath and advanced through the vasculature. Note in the embodiment of FIG. 2D, the guide catheter 150' has a side arm 152 for aspiration. However, alternatively a guide catheter without a side arm can be utilized in conjunction with a RHV with a side arm for aspiration as in the embodiment of FIG. 2A.

The guidewire is removed and a smaller diameter guidewire, e.g. 0.014 inch diameter, and the introducer catheter 300 are inserted through the guide catheter 150' and access sheath with the guidewire G in the femoral artery F and located via imaging. The introducer catheter 300 is advanced to the desired site through the vascular system into the cerebral arteries A, for example through the Circle of Willis (see FIG. 2D). Once at the site, the guidewire is withdrawn. Note the introducer catheter 300 is preferably inserted with the RHV 240 attached. That is, the tubular portion 246 of the RHV 240 is inserted through the introducer catheter 300 and attached thereto by rotation of cap 251.

Note in an alternate embodiment, instead of the RHV 240 attached prior to introduction of the introducer catheter 300 through the guide catheter, it can be attached after introduction of catheter 300 through the guide catheter.

The introducer sheath 260 is inserted through the RHV 240, and attached to the RHV 240 by rotation of cap 258 as shown in FIG. 2C. The thrombectomy wire 230 is inserted through the lumen of the introducer sheath 260, through the lumen of the RHV 240 and into the lumen of the introducer catheter 300. The introducer catheter 300 extends from the guide catheter 150' as shown in FIG. 2D, but the wire 230 remains inside the introducer catheter 300. The distal end of the wire 230 is then exposed from the introducer catheter 300 at the target surgical site by relative movement of the wire and introducer sheath 300. Note the wire 230 can be attached to the motor drive shaft 215 at this point or can be attached before exposed or at any other time in the procedure such as prior to insertion of the wire 230 through the introducer sheath 260. Attachment is achieved by connection of the connector tube 280 to the introducer sheath 260 and attachment of the proximal end of the connector 280 to the motor housing 212. The wire 230 extends through the connector tube and extends through connector 280 to the motor drive shaft 215. As noted above, alternatively, the connector tube 280 can be connected to the introducer sheath 260 prior to attachment to the motor housing 212, or alternatively connected after the wire 230 is at the surgical site and exposed from the introducer sheath.

With the wire 230 exposed from the introducer catheter 300, switch 219 on housing 122 is actuated to turn on the motor 214 thereby causing wire 230 to rotate about its longitudinal axis to break up/macerate thrombus.

To aspirate macerated particles, the pump 54 is turned on by switch 16. This aspirates the macerated particles through side arm 256 of RHV 240 as the particles travel in the space between wire 230 and introducer catheter 300 and RHV 240. Larger particles can be aspirated through the space between the guide catheter 150 (or 150') and introducer catheter 300. Aspirated particles travel through the respective RHV sides ports, into the respective tubing and into chamber 55. The pump 54 further pumps the aspirated particles from chamber 55 through the bag tubing 80 and into collection bag 21 as described above. Note introducer catheter 300 can optionally have a side port(s) and/or the guide catheter 150 can optionally have a side port(s) such as side port 152 for aspirating the small macerated particles in addition to or as an alternative to a side arm of an RHV.

The delivery (access) sheath or delivery catheter can optionally include a balloon (not shown) to block blood flow and allow aspiration in the blocked space.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An aspiration system for aspirating particles from a patient's body, the aspiration system comprising:
   a housing containing an aspiration pump and a chamber, the chamber configured to contain particles aspirated from the body;
   a collection bag;
   a tubing assembly having opposite first and second end portions, the tubing assembly being configurable in a shipping configuration, in which a first tube of the tubing assembly is wound into a first concentric coil and a second tube of the tubing assembly is wound into a second concentric coil, and the first and second end portions extend radially outward from the first and second concentric coils respectively and into the housing through a sidewall thereof, the tubing assembly fluidly connects the chamber and the collection bag so that particles are moved out of the chamber and into the collection bag, wherein the first concentric coil and the second concentric coil define a radial dimension such that in the shipping configuration, the tubing assembly is positionable underneath the housing and the first and second end portions are extendable into the housing; and
   an indicator to provide an indication to the user that the collection bag is full to prevent over expansion of the collection bag.

2. The aspiration system of claim 1, wherein the indicator is an LED indicator.

3. The aspiration system of claim 1, wherein the indicator is a shut off of the aspiration pump.

4. The aspiration system of claim 1, further comprising a controller positioned within the housing, wherein the controller detects back pressure when the collection bag is full.

5. The aspiration system of claim 4, wherein the controller sends a signal to the aspiration pump to turn off the aspiration pump if the hag is full.

6. The aspiration system of claim 4, wherein the controller sends a signal to the aspiration pump if a back pressure measurement rises to a predetermined amount.

7. The aspiration system of claim 1, wherein the collection bag is configured for shipping in a substantially flattened position underneath the housing and the tubing assembly such that the housing, the tubing assembly, and the collection bag are arranged in a vertical stack.

8. The aspiration system of claim 1, further comprising a non-conductive tab, the tab blocking electrical connection between components in the housing to prevent actuation of the aspiration pump, wherein the tab is removable to enable electrical connection of the components to enable actuation of the aspiration pump.

9. The aspiration system of claim 7, wherein the collection bag is configured for positioning underneath the tubing assembly such that the tubing assembly is interposed between the housing and the collection bag.

10. The aspiration system of claim 1, wherein the housing is positionable on a table during use.

11. An aspiration system for aspirating particles from a patient's body, the aspiration system comprising:
    a housing containing a chamber, an electrical subassembly and a power pack, the electrical subassembly including a controller and an aspiration pump, the chamber configured to contain particles aspirated from the body, the housing being portable and positionable on a table;
    a collection bag; and
    a tubing assembly having opposite first and second end portions, the tubing assembly being configurable in a shipping configuration in which a first tube of the tubing assembly is wound into a first concentric coil and a second tube of the tubing assembly is wound into a second concentric coil, and the first and second end portions extend radially outward from the first and second concentric coils respectively and into the housing through a sidewall thereof, the tubing assembly fluidly connects the chamber and the collection bag so that particles are moved out of the chamber and into the collection bag, the collection bag positioned outside the housing, wherein the first concentric coil and the second concentric coil define a radial dimension by such that, in the shipping configuration, the tubing assembly is positionable underneath the housing and the first and second end portions are extendable into the housing.

12. The aspiration system of claim 11, wherein the controller sends a signal to shut off the aspiration pump if backpressure in the collection bag reaches a predetermined amount.

13. The aspiration system of claim 11, wherein the collection bag and the housing including the chamber, electrical subassembly, and power pack are disposable.

14. The aspiration system of claim 1, further comprising a power pack containing one or more batteries, the power pack positioned in the housing.

15. The aspiration system of claim 11, wherein the housing is configured to be discarded after use.

16. The aspiration system of claim 11, wherein the power pack contains one or more batteries.

17. The aspiration system of claim 11, wherein the collection bag is configured for shipping in a substantially flattened position underneath the housing and the tubing assembly such that the housing, the tubing assembly, and the collection bag are arranged in a vertical stack.

18. The aspiration system of claim 17, the collection bag is configured for positioning underneath the tubing assembly such that the tubing assembly is interposed between the housing and the collection bag.

19. The aspiration system of claim 1, wherein the first concentric coil and the second concentric coil have a radial dimension corresponding to a radial dimension of the housing.

* * * * *